United States Patent
Lunner et al.

(10) Patent No.: US 11,297,448 B2
(45) Date of Patent: Apr. 5, 2022

(54) PORTABLE SYSTEM FOR GATHERING AND PROCESSING DATA FROM EEG, EOG, AND/OR IMAGING SENSORS

(71) Applicant: Oticon A/S, Smørum (DK)

(72) Inventors: Thomas Lunner, Smørum (DK); Alejandro Lopez Valdes, Smørum (DK); Henrik Bendsen, Smørum (DK); Claus Christensen, Smørum (DK); Peter Schmidt, Haderslev (DK); Ole Andersen, Smørum (DK); Mikkel Nielsen, Smørum (DK); Tanveer Bhuiyan, Smørum (DK)

(73) Assignee: OTICON A/S, Smørum (DK)

( * ) Notice: Subject to any disclaimer, the term of this patent is extended or adjusted under 35 U.S.C. 154(b) by 34 days.

(21) Appl. No.: 16/750,854

(22) Filed: Jan. 23, 2020

(65) Prior Publication Data
US 2021/0235203 A1 Jul. 29, 2021

(51) Int. Cl.
*H04R 25/00* (2006.01)
*G06F 3/01* (2006.01)
(Continued)

(52) U.S. Cl.
CPC .......... *H04R 25/552* (2013.01); *A61B 5/163* (2017.08); *A61B 5/398* (2021.01); *A61B 5/4023* (2013.01); *A61B 5/4812* (2013.01); *G06F 3/013* (2013.01); *G06F 3/015* (2013.01); *H04R 3/005* (2013.01); *H04R 25/505* (2013.01);
(Continued)

(58) Field of Classification Search
None
See application file for complete search history.

(56) References Cited

U.S. PATENT DOCUMENTS

| | | | |
|---|---|---|---|
| 9,579,060 B1* | 2/2017 | Lisy | A61B 5/302 |
| 2007/0112277 A1* | 5/2007 | Fischer | A61B 5/0006 600/544 |

(Continued)

FOREIGN PATENT DOCUMENTS

EP 3 185 590 A1 6/2017

OTHER PUBLICATIONS

Zhang et al., "Continuous Vigilance Estimation Using LSTM Neural Networks," International Conference on Neural Information Processing, Part II, vol. 9948, 2016, pp. 530-537.

*Primary Examiner* — Walter F Briney, III
(74) *Attorney, Agent, or Firm* — Birch, Stewart, Kolasch & Birch, LLP

(57) ABSTRACT

A method for picking up body signals from the head of a user comprises a) placing first and second electrodes on first and second different positions at a first side of the user's head in direct or capacitive contact with the user's head, said first side comprising a first eye of the user, the first and second electrodes being configured to pick up first and second electric potentials, respectively, from the user's body, and b) providing an Electrooculography signal representative of a corneo-retinal potential difference of said first eye of the user in dependence of said at first and second electric potentials. The first and second positions may be (substantially) located in a plane including the first eye of the user. A portable electronic device providing an Electrooculography signal, and a hearing device utilizing an Electrooculography signal is further disclosed.

22 Claims, 11 Drawing Sheets

(51) Int. Cl.
*A61B 5/16* (2006.01)
*A61B 5/00* (2006.01)
*H04R 3/00* (2006.01)
*A61B 5/398* (2021.01)

(52) U.S. Cl.
CPC ......... *H04R 25/604* (2013.01); *H04R 25/609* (2019.05); *H04R 2225/55* (2013.01); *H04R 2225/67* (2013.01)

(56) References Cited

U.S. PATENT DOCUMENTS

| | | | |
|---|---|---|---|
| 2011/0077548 A1* | 3/2011 | Torch | A61B 5/165 600/558 |
| 2014/0140567 A1* | 5/2014 | LeBoeuf | A61B 5/1118 381/381 |
| 2015/0126845 A1* | 5/2015 | Jin | G06F 3/013 600/383 |
| 2016/0077547 A1* | 3/2016 | Aimone | A61B 5/0022 345/8 |
| 2016/0270656 A1* | 9/2016 | Samec | A61B 3/102 |
| 2017/0311097 A1* | 10/2017 | Nielsen | A61N 1/0541 |
| 2018/0368722 A1* | 12/2018 | Lu | A61B 5/291 |
| 2019/0174237 A1* | 6/2019 | Lunner | H04R 25/43 |
| 2019/0223747 A1* | 7/2019 | Chou | A61B 5/681 |

* cited by examiner (a) Traditional EOG  (b) Forehead EOG

PORTABLE SYSTEM FOR GATHERING AND PROCESSING DATA FROM EEG, EOG, AND/OR IMAGING SENSORS

SUMMARY

The present application relates to various aspects of the capture of electrooculography (EOG), in particular in connection with portable electronic devices (wearables, e.g. ear buds), e.g. hearing devices (hearables, e.g. hearing aids or headsets).

A Method:

In an aspect of the present application, a method for picking up body signals from the head of a user is provide. The method comprises placing first and second electrodes on first and second different positions at a first side of the user's head in direct or capacitive contact with the user's head, said first side comprising a first eye of the user, the first and second electrodes being configured to pick up first and second electric potentials, respectively, from the user's body. The method may further comprise, providing an Electrooculography signal representative of a corneo-retinal potential difference of said first eye of the user in dependence of said at first and second electric potentials.

Thereby a simplified estimate of an eye gaze of the user may be provided.

The first and second electrodes are unilaterally located. An electric dipole is created from the cornea (front part of the eye comprising the pupil, iris and eye liquid, being the positive pole) to the retina (rear part of the eye comprising the eye nerve, being the negative pole). The term 'corneo-retinal potential difference' is taken to be the difference between the electric potentials of the positive pole (of cornea) and the negative pole (of retina), respectively.

The first and second electrodes may be placed in a direction (e.g. a plane) of eye movements of interest to be monitored. The first and second electrodes may e.g. be located in a plane of horizontal eye movements (left-right) (when the user is in an upright position) to thereby be suited for acquiring EOG signals (representing horizontal eye gaze), and correspondingly in a vertical plane for monitoring vertical eye gaze. The first and second positions may be (substantially) located in a plane including the first eye of the user. The user's head may be divided in a first side and a second side, e.g. separated by a symmetry plane through the nose. So that a first side e.g. comprises a first (e.g. left) eye and ear and a second side comprises a second (e.g. right) eye and ear of the user. The first and second positions may be located (substantially) in a plane through the first and second eyes of the user.

The first position may be closer to the first eye than the second position. The first and second positions may be on each side of the ear. The first position may be on the front side of the ear (pinna) and the second position may be on the rear side of the ear (pinna), see e.g. FIG. 5 (right). A horizontal plane may e.g. be defined by a plane including the user's eyes, horizontal being defined by being perpendicular to the force of gravity. The horizontal plane may e.g. be defined by a plane through the user's eyes and ears of the user.

The first and second electrodes may be capacitively coupled electrodes. The capacitively coupled electrodes are coupled to the head of the user via a dielectric material in contact with the user's head (e.g. skin). A capacitively coupled electrode may e.g. form part of an electric potential sensor (EPS), see e.g. FIG. 1 in [3].

The first and second electrodes are direct contact electrodes. The direct contact electrodes are in direct contact with the head (e.g. skin) of the user. A direct contact electrode may e.g. be an AgCl electrode. The first and second electrodes may e.g. comprise different kinds of electrodes, e.g. at least two of a capacitively coupled electrode, a direct coupled electrode and an inductively coupled electrode.

The first and/or second electrodes may be implanted in the head of the user, e.g. between skin and tissue, or between tissue and skull of the user.

The first and second positions are located a minimum distance $L_{12,min}$ from each other. For a given position of the first electrode (e.g. located closer to the first eye than the second electrode), the difference in electric potential between the first and second electrodes decreases with increasing distance $L_{12}$ between the first and second electrodes. The electrodes may preferably be calibrated to determine the sensitivity of the electric potential picked up by the second electrode to its distance from the first electrode, see e.g. FIG. 6, 7. Preferably, the minimum distance between the first and second electrodes when located on the user's head is in the range between 3 cm and 5 cm, e.g. 4 cm. The distance between the first and second electrodes may e.g. be measured along the surface (skin) of the (first side of the) head of the user.

A Portable Electronic Device:

In an aspect, a portable electronic device is provided. The portable electronic device comprises first and second electrodes configured to be located on first and second different positions at a first side of the user's head in direct or capacitive contact with the user's head. The first side may comprise a first eye of the user. The first and second electrodes may be configured to pick up first and second electric potentials, respectively, from the user's body. The portable electronic device may further comprise a processor electrically connected to said first and second electrodes and configured to provide an Electrooculography signal representative of a corneo-retinal potential difference of said first eye of the user in dependence of the first and second electric potentials.

It is intended that some or all of the processing features of the method described above, in the 'detailed description of embodiments' or in the claims can be combined with embodiments of the device, when appropriately substituted by a corresponding structural features and vice versa. Embodiments of the device have the same advantages as the corresponding method.

The processor may be directly (e.g. galvanically) electrically connected to said first and second electrodes. This has the advantage that the transmission of the individual potentials from one ear to the other can be dispensed with. The processor may comprise an AD-converter, or an AD-converter may be located between the electrodes and the processor.

The first and second positions may be (substantially) located in a plane including the first eye of the user. The first and second positions may be located (substantially) in a plane through the first and second eyes of the user.

The portable electronic device may be configured to use the Electrooculography signal to monitor eye movements of the user.

The portable electronic device may be configured to monitor one or more of a user's Vigilance, Balance disorder, and Sleep.

The portable electronic device may comprise antenna and transceiver circuitry configured to transmit said Electrooculography signal or a signal derived therefrom to another device or system. The portable electronic device may thus facilitate the control of another device by the eye gaze of the user wearing the portable electronic device. The 'another device' may be configured to further process (e.g. improve the quality or confidence of) the Electrooculography signal delivered by the portable electronic device.

The portable device may comprise a head-worn frame, e.g. for supporting glasses, and/or one or more sensors, e.g. an acoustic or light-based image sensor, e.g. a camera.

A Hearing Device:

In an aspect, a hearing device comprising or forming part of a portable electronic device as described above, in the 'detailed description of embodiments' or in the claims is furthermore provided. The hearing device, e.g. a hearing aid, may be configured to be located in or at an ear of a user or to be partially or fully implanted in the head of the user. The hearing device may comprise
- an input unit comprising an input transducer configured to pick up sound from the environment of the user and to provide an electric input signal representative of said sound; and
- an output unit configured to present stimuli perceivable to the user as representing said sound or a processed version thereof.

Functionality of the hearing device may be partially or fully controlled by the Electrooculography signal.

The hearing device may comprise the processor of the portable electronic device.

The input unit may comprise at least two input transducers configured to pick up sound from the environment of the user and to provide respective at least two electric input signals. The hearing device may further comprise a processor for processing the at least two electric input signals. The processor may comprise a beamformer for providing a beamformed signal based on the at least two electric input signals. The processor may be configured to partially or fully control the beamformed signal in dependence of the Electrooculography signal. Thereby directionality of the hearing device can be steered by the unilaterally located electrodes based on the user's eye gaze. The processor of the hearing device may form part of or comprise the processor (or the portable electronic device) for determining the Electrooculography signal.

The processor of the hearing device may be separate from the processor for determining the Electrooculography signal.

The hearing device may comprise a further electrode located in or on a housing of the hearing device. The hearing device may comprise an ITE-part adapted for being located at or in an ear canal of the user. The ITE-part may comprise a separate housing. The further electrode may be located in or on the housing of the ITE-part. The hearing device may additionally or alternatively comprise a BTE-part adapted for being located at or behind an ear (pinna) of the user. The BTE-part may comprise a separate housing. The further electrode may be located in or on the housing of the BTE-part. The ITE-part and the BTE-part may be connected, e.g. acoustically or electrically connected.

The hearing device may be constituted by or comprise a hearing aid, a headset, an earphone, an ear protection device or a combination thereof.

The hearing device may be constituted by or comprise an air-conduction type hearing aid, a bone-conduction type hearing aid, a cochlear implant type hearing aid, or a combination thereof.

The hearing device may be adapted to provide a frequency dependent gain and/or a level dependent compression and/or a transposition (with or without frequency compression) of one or more frequency ranges to one or more other frequency ranges, e.g. to compensate for a hearing impairment of a user. The hearing device may comprise a signal processor for enhancing the input signals and providing a processed output signal.

The hearing device comprises an output unit for providing a stimulus perceived by the user as an acoustic signal based on a processed electric signal. The output unit may comprise a number of electrodes of a cochlear implant (for a CI type hearing device) or a vibrator of a bone conducting hearing device. The output unit may comprise an output transducer. The output transducer may comprise a receiver (loudspeaker) for providing the stimulus as an acoustic signal to the user (e.g. in an acoustic (air conduction based) hearing device). The output transducer may comprise a vibrator for providing the stimulus as mechanical vibration of a skull bone to the user (e.g. in a bone-attached or bone-anchored hearing device).

The hearing device comprises an input unit for providing an electric input signal representing sound. The input unit may comprise an input transducer, e.g. a microphone, for converting an input sound to an electric input signal. The input unit may comprise a wireless receiver for receiving a wireless signal comprising or representing sound and for providing an electric input signal representing said sound. The wireless receiver may e.g. be configured to receive an electromagnetic signal in the radio frequency range (3 kHz to 300 GHz). The wireless receiver may e.g. be configured to receive an electromagnetic signal in a frequency range of light (e.g. infrared light 300 GHz to 430 THz, or visible light, e.g. 430 THz to 770 THz).

The hearing device may comprise a directional microphone system adapted to spatially filter sounds from the environment, and thereby enhance a target acoustic source among a multitude of acoustic sources in the local environment of the user wearing the hearing device. The directional system is adapted to detect (such as adaptively detect) from which direction a particular part of the microphone signal originates. This can be achieved in various different ways as e.g. described in the prior art. In hearing devices, a microphone array beamformer is often used for spatially attenuating background noise sources. Many beamformer variants can be found in literature. The minimum variance distortionless response (MVDR) beamformer is widely used in microphone array signal processing. Ideally the MVDR beamformer keeps the signals from the target direction (also referred to as the look direction) unchanged, while attenuating sound signals from other directions maximally The generalized sidelobe canceller (GSC) structure is an equivalent representation of the MVDR beamformer offering computational and numerical advantages over a direct implementation in its original form.

The hearing device may comprise antenna and transceiver circuitry (e.g. a wireless receiver) for wirelessly receiving a direct electric input signal from another device, e.g. from an entertainment device (e.g. a TV-set), a communication device, a wireless microphone, or another hearing device. The direct electric input signal may represent or comprise an audio signal and/or a control signal and/or an information signal The hearing device may comprise demodulation circuitry for demodulating the received direct electric input to provide the direct electric input signal representing an audio signal and/or a control signal e.g. for setting an operational parameter (e.g. volume) and/or a processing parameter of the hearing device. In general, a wireless link established by antenna and transceiver circuitry of the hearing device can be of any type. The communication between the hearing device and the other device may be in the base band (audio frequency range, e.g. between 0 and 20 kHz). Preferably, communication between the hearing device and the other device is based on some sort of modulation at frequencies above 100 kHz. Preferably, frequencies used to establish a communication link between the hearing device and the other device is below 70 GHz, e.g. located in a range from 50 MHz to 70 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). The wireless link may be based on a standardized or proprietary technology. The wireless link may be based on Bluetooth technology (e.g. Bluetooth Low-Energy technology).

The hearing device may have a maximum outer dimension of the order of 0.15 m (e.g. a handheld mobile telephone). The hearing device may have a maximum outer dimension of the order of 0.08 m (e.g. a headset). The hearing device may have a maximum outer dimension of the order of 0.04 m (e.g. a hearing instrument).

The hearing device may be or form part of a portable (i.e. configured to be wearable) device, e.g. a device comprising a local energy source, e.g. a battery, e.g. a rechargeable battery. The hearing device may e.g. be a low weight, easily wearable, device, e.g. having a total weight less than 100 g, e.g. less than 20 g.

The hearing device may comprise a forward or signal path between an input unit (e.g. an input transducer, such as a microphone or a microphone system and/or direct electric input (e.g. a wireless receiver)) and an output unit, e.g. an output transducer. The signal processor may be located in the forward path. The signal processor may be adapted to provide a frequency dependent gain according to a user's particular needs. The hearing device may comprise an analysis path comprising functional components for analyzing the input signal (e.g. determining a level, a modulation, a type of signal, an acoustic feedback estimate, etc.). Some or all signal processing of the analysis path and/or the signal path may be conducted in the frequency domain. Some or all signal processing of the analysis path and/or the signal path may be conducted in the time domain.

An analogue electric signal representing an acoustic signal may be converted to a digital audio signal in an analogue-to-digital (AD) conversion process, where the analogue signal is sampled with a predefined sampling frequency or rate $f_s$, $f_s$ being e.g. in the range from 8 kHz to 48 kHz (adapted to the particular needs of the application) to provide digital samples $x_n$ (or x[n]) at discrete points in time $t_n$ (or n), each audio sample representing the value of the acoustic signal at $t_n$ by a predefined number $N_b$ of bits, $N_b$ being e.g. in the range from 1 to 48 bits, e.g. 24 bits. Each audio sample is hence quantized using $N_b$ bits (resulting in $2^{Nb}$ different possible values of the audio sample). A digital sample x has a length in time of $1/f_s$, e.g. 50 µs, for $f_s$=20 kHz. A number of audio samples may be arranged in a time frame. A time frame may comprise 64 or 128 audio data samples. Other frame lengths may be used depending on the practical application.

The hearing device may comprise an analogue-to-digital (AD) converter to digitize an analogue input (e.g. from an input transducer, such as a microphone) with a predefined sampling rate, e.g. 20 kHz. The hearing devices may comprise a digital-to-analogue (DA) converter to convert a digital signal to an analogue output signal, e.g. for being presented to a user via an output transducer.

The hearing device, e.g. the input unit, and or the antenna and transceiver circuitry comprise(s) a TF-conversion unit for providing a time-frequency representation of an input signal. The time-frequency representation may comprise an array or map of corresponding complex or real values of the signal in question in a particular time and frequency range. The TF conversion unit may comprise a filter bank for filtering a (time varying) input signal and providing a number of (time varying) output signals each comprising a distinct frequency range of the input signal. The TF conversion unit may comprise a Fourier transformation unit for converting a time variant input signal to a (time variant) signal in the (time-)frequency domain. The frequency range considered by the hearing device from a minimum frequency $f_{min}$ to a maximum frequency $f_{max}$ may comprise a part of the typical human audible frequency range from 20 Hz to 20 kHz, e.g. a part of the range from 20 Hz to 12 kHz. Typically, a sample rate $f_s$ is larger than or equal to twice the maximum frequency $f_{max}$, $f_s \geq 2f_{max}$. A signal of the forward and/or analysis path of the hearing device may be split into a number NI of frequency bands (e.g. of uniform width), where NI is e.g. larger than 5, such as larger than 10, such as larger than 50, such as larger than 100, such as larger than 500, at least some of which are processed individually. The hearing device may be adapted to process a signal of the forward and/or analysis path in a number NP of different frequency channels (NP ≤NI). The frequency channels may be uniform or non-uniform in width (e.g. increasing in width with frequency), overlapping or non-overlapping.

The hearing device may be configured to operate in different modes, e.g. a normal mode and one or more specific modes, e.g. selectable by a user, or automatically selectable. A mode of operation may be optimized to a specific acoustic situation or environment. A mode of operation may include a low-power mode, where functionality of the hearing device is reduced (e.g. to save power), e.g. to disable wireless communication, and/or to disable specific features of the hearing device.

The hearing device may comprise a number of detectors configured to provide status signals relating to a current physical environment of the hearing device (e.g. the current acoustic environment), and/or to a current state of the user wearing the hearing device, and/or to a current state or mode of operation of the hearing device. Alternatively, or additionally, one or more detectors may form part of an external device in communication (e.g. wirelessly) with the hearing device. An external device may e.g. comprise another hearing device, a remote control, and audio delivery device, a telephone (e.g. a smartphone), an external sensor, etc.

One or more of the number of detectors may operate on the full band signal (time domain) One or more of the number of detectors may operate on band split signals ((time-) frequency domain), e.g. in a limited number of frequency bands.

The number of detectors may comprise a level detector for estimating a current level of a signal of the forward path. The detector may be configured to decide whether the current level of a signal of the forward path is above or below a given (L-)threshold value. The level detector operates on the full band signal (time domain). The level detector operates on band split signals ((time-) frequency domain)

The hearing device may comprise a voice activity detector (VAD) for estimating whether or not (or with what probability) an input signal comprises a voice signal (at a given point in time). A voice signal is in the present context taken to include a speech signal from a human being. It may also include other forms of utterances generated by the human speech system (e.g. singing). The voice activity detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only (or mainly) comprising other sound sources (e.g. artificially generated noise). The voice activity detector may be adapted to detect as a VOICE also the user's own voice. Alternatively, the voice activity detector may be adapted to exclude a user's own voice from the detection of a VOICE.

The hearing device may comprise an own voice detector for estimating whether or not (or with what probability) a given input sound (e.g. a voice, e.g. speech) originates from the voice of the user of the system. A microphone system of the hearing device may be adapted to be able to differentiate between a user's own voice and another person's voice and possibly from NON-voice sounds.

The number of detectors may comprise a movement detector, e.g. an acceleration sensor. The movement detector is configured to detect movement of the user's facial muscles and/or bones, e.g. due to speech or chewing (e.g. jaw movement) and to provide a detector signal indicative thereof.

The hearing device may comprise a classification unit configured to classify the current situation based on input signals from (at least some of) the detectors, and possibly other inputs as well. In the present context 'a current situation' is taken to be defined by one or more of a) the physical environment (e.g. including the current electromagnetic environment, e.g. the occurrence of electromagnetic signals (e.g. comprising audio and/or control signals) intended or not intended for reception by the hearing device, or other properties of the current environment than acoustic);

b) the current acoustic situation (input level, feedback, etc.), and c) the current mode or state of the user (movement, temperature, cognitive load, etc.);

d) the current mode or state of the hearing device (program selected, time elapsed since last user interaction, etc.) and/or of another device in communication with the hearing device.

The classification unit may be based on or comprise a neural network, e.g. a rained neural network.

The hearing device may further comprise other relevant functionality for the application in question, e.g. compression, noise reduction, feedback control, etc.

The hearing device may comprise a listening device, e.g. a hearing aid, e.g. a hearing instrument, e.g. a hearing instrument adapted for being located at the ear or fully or partially in the ear canal of a user, e.g. a headset, an earphone, an ear protection device or a combination thereof. The hearing assistance system may comprise a speakerphone (comprising a number of input transducers and a number of output transducers, e.g. for use in an audio conference situation), e.g. comprising a beamformer filtering unit, e.g. providing multiple beamforming capabilities.

Use:

In an aspect, use of a hearing device as described above, in the 'detailed description of embodiments' and in the claims, is moreover provided. Use may be provided in a system comprising audio distribution. Use may be provided in a system comprising one or more hearing aids (e.g. hearing instruments), headsets, ear phones, active ear protection systems, etc., e.g. in handsfree telephone systems, teleconferencing systems (e.g. including a speakerphone), public address systems, karaoke systems, classroom amplification systems, etc. Use of a hearing device for controlling functionality of the hearing device or another device or system by means of eye gaze of the user wearing the hearing device.

A Hearing System:

In a further aspect, a hearing system comprising a hearing device as described above, in the 'detailed description of embodiments', and in the claims, AND an auxiliary device is moreover provided.

The hearing system may be adapted to establish a communication link between the hearing device and the auxiliary device to provide that information (e.g. control and status signals, possibly audio signals) can be exchanged or forwarded from one to the other.

The auxiliary device may comprise a remote control, a smartphone, or other portable or wearable electronic device, such as a smartwatch or the like.

The auxiliary device may be constituted by or comprise a remote control for controlling functionality and operation of the hearing device(s). The function of a remote control is implemented in a smartphone, the smartphone possibly running an APP allowing to control the functionality of the audio processing device via the smartphone (the hearing device(s) comprising an appropriate wireless interface to the smartphone, e.g. based on Bluetooth or some other standardized or proprietary scheme).

The auxiliary device may be constituted by or comprise an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing device.

The auxiliary device may be constituted by or comprise another hearing device. The hearing system may comprise two hearing devices adapted to implement a binaural hearing system, e.g. a binaural hearing aid system.

The binaural hearing system may comprise first and second hearing devices as claimed as described above, in the 'detailed description of embodiments' and in the claims, wherein the first and second hearing devices are configured to be able to exchange data between each other. Thereby a binaural hearing aid system based on sound signals and/or EOG signals from both sides of the user's head can be provided.

An APP:

In a further aspect, a non-transitory application, termed an APP, is furthermore provided by the present disclosure. The APP comprises executable instructions configured to be executed on an auxiliary device to implement a user interface for a hearing device or a hearing system described above in the 'detailed description of embodiments', and in the claims. The APP is configured to run on cellular phone, e.g. a smartphone, or on another portable device allowing communication with said hearing device or said hearing system.

Definitions:

In the present context, a 'hearing device' refers to a device, such as a hearing aid, e.g. a hearing instrument, or an active ear-protection device, or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with an output transducer, e.g. a loudspeaker, arranged close to or in the ear canal, as a unit entirely or partly arranged in the pinna and/or in the ear canal, as a unit, e.g. a vibrator, attached to a fixture implanted into the skull bone, as an attachable, or entirely or partly implanted, unit, etc. The hearing device may comprise a single unit or several units communicating (e.g. acoustically, electrically or optically) with each other. The loudspeaker may be arranged in a housing together with other components of the hearing device, or may be an external unit in itself (possibly in combination with a flexible guiding element, e.g. a dome-like element).

More generally, a hearing device comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit (e.g. a signal processor, e.g. comprising a configurable (programmable) processor, e.g. a digital signal processor) for processing the input audio signal and an output unit for providing an audible signal to the user in dependence on the processed audio signal. The signal processor may be adapted to process the input signal in the time domain or in a number of frequency bands. In some hearing devices, an amplifier and/or compressor may constitute the signal processing circuit. The signal processing circuit typically comprises one or more (integrated or separate) memory elements for executing programs and/or for storing parameters used (or potentially used) in the processing and/or for storing information relevant for the function of the hearing device and/or for storing information (e.g. processed information, e.g. provided by the signal processing circuit), e.g. for use in connection with an interface to a user and/or an interface to a programming device. In some hearing devices, the output unit may comprise an output transducer, such as e.g. a loudspeaker for providing an air-borne acoustic signal or a vibrator for providing a structure-borne or liquid-borne acoustic signal. In some hearing devices, the output unit may comprise one or more output electrodes for providing electric signals (e.g. to a multi-electrode array) for electrically stimulating the cochlear nerve (cochlear implant type hearing aid). The hearing device may comprise a speakerphone (comprising a number of input transducers and a number of output transducers), e.g. for use in an audio conference situation.

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A hearing device, e.g. a hearing aid, may be adapted to a particular user's needs, e.g. a hearing impairment. A configurable signal processing circuit of the hearing device may be adapted to apply a frequency and level dependent compressive amplification of an input signal. A customized frequency and level dependent gain (amplification or compression) may be determined in a fitting process by a fitting system based on a user's hearing data, e.g. an audiogram, using a fitting rationale (e.g. adapted to speech). The frequency and level dependent gain may e.g. be embodied in processing parameters, e.g. uploaded to the hearing device via an interface to a programming device (fitting system), and used by a processing algorithm executed by the configurable signal processing circuit of the hearing device.

A 'hearing system' refers to a system comprising one or two hearing devices, and a 'binaural hearing system' refers to a system comprising two hearing devices and being adapted to cooperatively provide audible signals to both of the user's ears. Hearing systems or binaural hearing systems may further comprise one or more 'auxiliary devices', which communicate with the hearing device(s) and affect and/or benefit from the function of the hearing device(s). Such auxiliary devices may include at least one of a remote control, a remote microphone, an audio gateway device, an entertainment device, e.g. a music player, a wireless communication device, e.g. a mobile phone (such as a smartphone) or a tablet or another device, e.g. comprising a graphical interface. Hearing devices, hearing systems or binaural hearing systems may e.g. be used for compensating for a hearing-impaired person's loss of hearing capability, augmenting or protecting a normal-hearing person's hearing capability and/or conveying electronic audio signals to a person. Hearing devices or hearing systems may e.g. form part of or interact with public-address systems, active ear protection systems, handsfree telephone systems, car audio systems, entertainment (e.g. TV, music playing or karaoke) systems, teleconferencing systems, classroom amplification systems, etc.

Embodiments of the disclosure may e.g. be useful in applications such as applications.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g. flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The present application relates to the field of hearing devices, e.g. hearing aids. The present application specifically relates to various aspects of capture of bio-signals from a persons' body, e.g. EEG signals or EOG signals.

Figure 1:
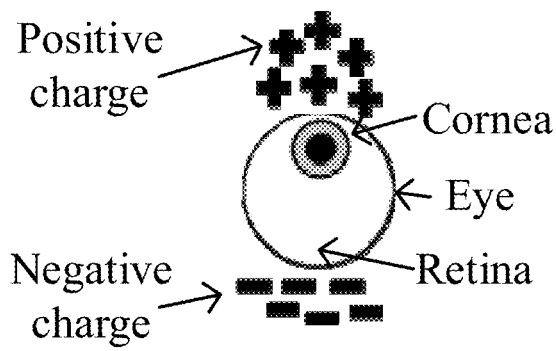
FIG. 1 schematically shows a natural eye dipole.

Capture of EOG Signals:

Due to the natural metabolism processes that happen in the eye, there is a small dipole created from the cornea (including the front part of the eye comprising the pupil, iris and eye liquid, being the positive pole) to Bruch's membrane between the retina and the sclera of the eye (rear part of the eye comprising the eye nerve, being the negative pole) as depicted in FIG. 1. FIG. 1 schematically illustrates electric properties of the eye as a natural eye dipole.

Figure 2:
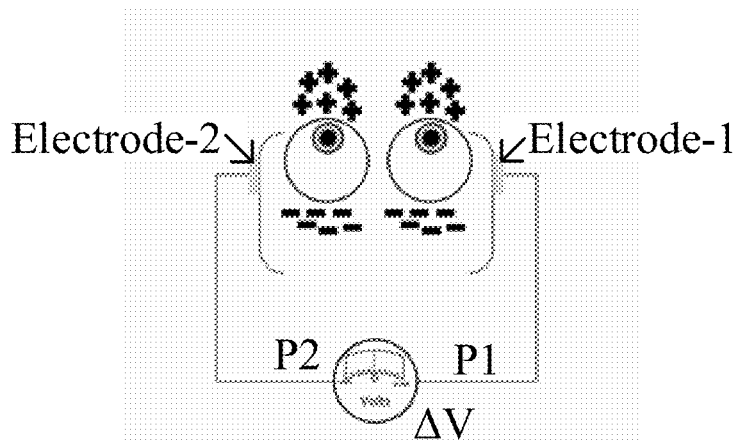
FIG. 2 schematically shows a setup for measurement of voltage deflections with horizontal eye movement using electrodes across the temples.

If a pair of electrodes (Electrode-1, Electrode-2) are placed across the temples of the head of a person, a voltage ($\Delta V = P2 - P1$) can be measured, which fluctuates proportionally to the movement of the person's eye balls in the horizontal plane (see FIG. 2). FIG. 2 schematically shows a setup for measurement of voltage deflections with horizontal eye movement using electrodes across the temples.

Figure 3:
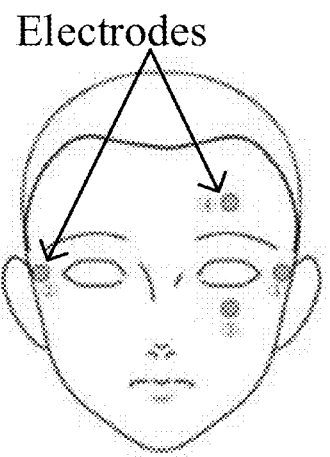
FIG. 3 shows LEFT: A traditional positioning of electrodes to measure horizontal and vertical EOG. RIGHT: Alternative forehead electrode positioning of electrodes to measure horizontal and vertical EOG, FIG. 4 schematically shows a measurement setup for measuring EOG using in-ear electrodes.
Figure 3:
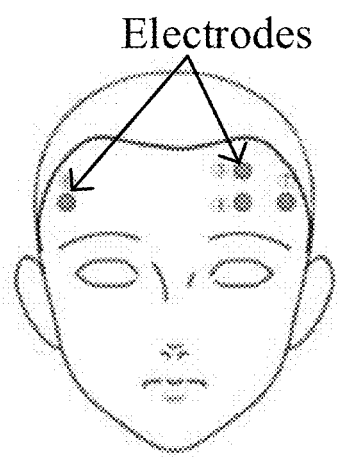

Measurements could also be performed in the vertical plane if we place the electrodes above and below the eyes see FIG. 3 left. This is what we call an EOG signal. Not only are we able to capture the EOG signal from electrodes across the temples of the head. It has been shown that these potentials can also be captured by placing electrodes on the forehead (see e.g. FIG. 3 right), however covering both sides of the head (i.e. bilaterally) [1]. FIG. 3 shows LEFT: A traditional positioning of electrodes to measure horizontal and vertical EOG. RIGHT: Alternative forehead electrode positioning of electrodes to measure horizontal and vertical EOG.

Figure 4:
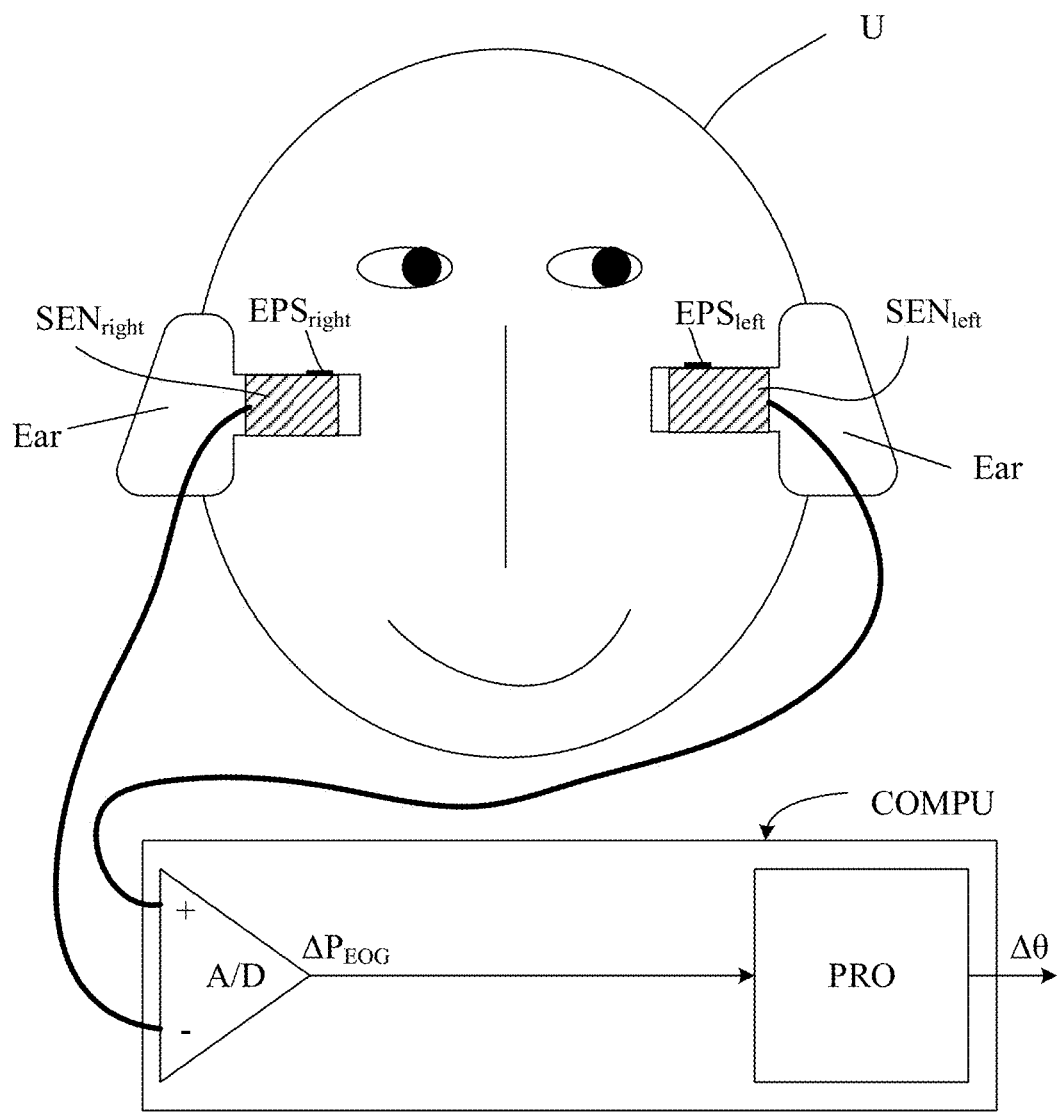

In a further configuration, electrodes are placed in the ear cavities [2] (see e.g. FIG. 4). FIG. 4 shows a measurement setup for measuring EOG using in-ear electrodes. FIG. 4 shows a configuration of an eye gaze estimation system worn by a user (U). The system comprises left and right sensor parts (SEN$_{left}$, SEN$_{right}$) adapted for being located at or in left and right ears (Ear) and/or for fully or partially being implanted in the head at left and right ears of a user. The left and right sensor parts comprise a left and a right electrical potential sensor (EPS$_{left}$, EPS$_{right}$), respectively, for sensing respective electrical potentials (P$_{left}$, P$_{right}$) from the user's head. The eye gaze estimation system further comprises electronic circuitry (COMPU) electrically coupled to the respective left and right electrical potential sensor parts (SEN$_{left}$, SEN$_{right}$) and configured to determine a single channel amplified output (ΔP) representative of a difference between the left and right electrical potentials. The single channel amplified output (ΔP) represents—at least in a specific electro-oculography (EOG) mode of operation—an EOG signal (ΔP$_{EOG}$). In the embodiment of FIG. 4, the electric circuitry comprises an analogue to digital converter A/D for providing an amplified, digitized version of the difference between the right and left electric potentials (P$_{left}$, P$_{right}$) provided by the respective left and right electrical potential sensors (EPS$_{left}$, EPS$_{right}$). The electronic circuitry (COMPU) further comprises a signal processor (PRO) configured to estimate an eye gaze angle (Δθ) based on the (possibly further processed, e.g. filtered) EOG signal (ΔP$_{EOG}$).

Monitoring eye movements is of interest for a variety of fields, some of which include:
 Vigilance monitoring
 Balance disorder diagnosis and management
 Steering directionality of hearing devices
 Sleep assessment.

However, the limitation of a bilateral placement of sensors on the head limits its practicality in portable, covert or discrete solutions, and prohibits its integration in ordinary hearing devices.

According to an aspect of the present disclosure, the electrodes are placed unilaterally on the head to capture EOG signals at different signal levels with different electrode variants such as Capacitive Electrodes or Contact electrodes.

Figure 5:
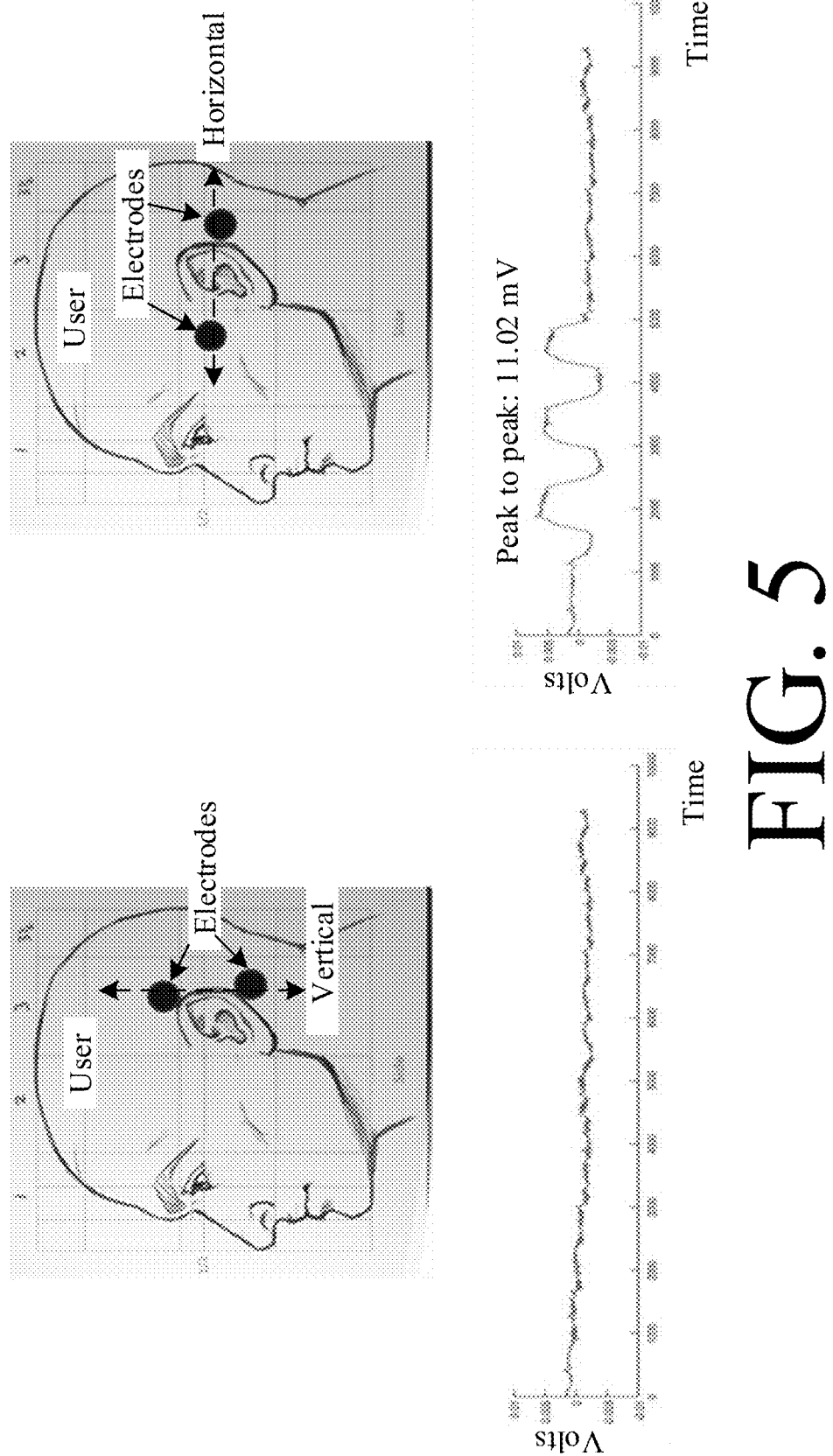
FIG. 5 illustrates two different unilateral electrode positions for measuring EOG, the LEFT part illustrating the electrodes placed on a line perpendicular to the plane of horizontal eye movement (top LEFT) and resulting in no EOG-signal being recorded (bottom LEFT), the RIGHT part illustrating the electrodes placed on a line in the plane of horizontal eye movement, resulting in a clear EOG-signal being recorded.

The electrodes are oriented towards the plane of the horizontal eye movements (left-right) to acquire the EOG signals. FIG. 5 shows two different unilateral electrode placements for measuring EOG (top) and corresponding EOG-signal [Volt] (scale between −0.01 V and +0.01 V) over samples of data acquired [time] (bottom graphs, scale between 0 and 10000; each sample is (1/f$_s$[Hz]) s, e.g. 1 ms, for f$_s$=1 kHz.). On the top left, the (two) electrodes are placed on the user's head (at an ear, one above, one below pinna) perpendicular to the plane of the eye movements (indicated by vertical double arrow) and as a result no horizontal EOG signal is recorded (cf. bottom left graph, comprising no clear structure). On the top right, the (two) electrodes are placed in the plane of the eye movements (indicated by horizontal double arrow, one on each side of pinna), and a clear EOG signal is recorded (cf. bottom right graph; exhibiting a clear pulse-like structure with a peak-to-peak voltage of 11 mV). Therefore, the placement of the electrodes should be in line with the eye movement of interest.

Not only the orientation of the electrodes plays a role in a successful measurement of unilateral EOG signals. The signal level is further dependent on the distance between the electrodes. The shorter the distance the smaller the signal level. The characterization of such distance scaling is an important design parameter for ear level devices where electrodes are intended to be in or around the ear and whose intended application is the acquisition EOG.

Figure 6:
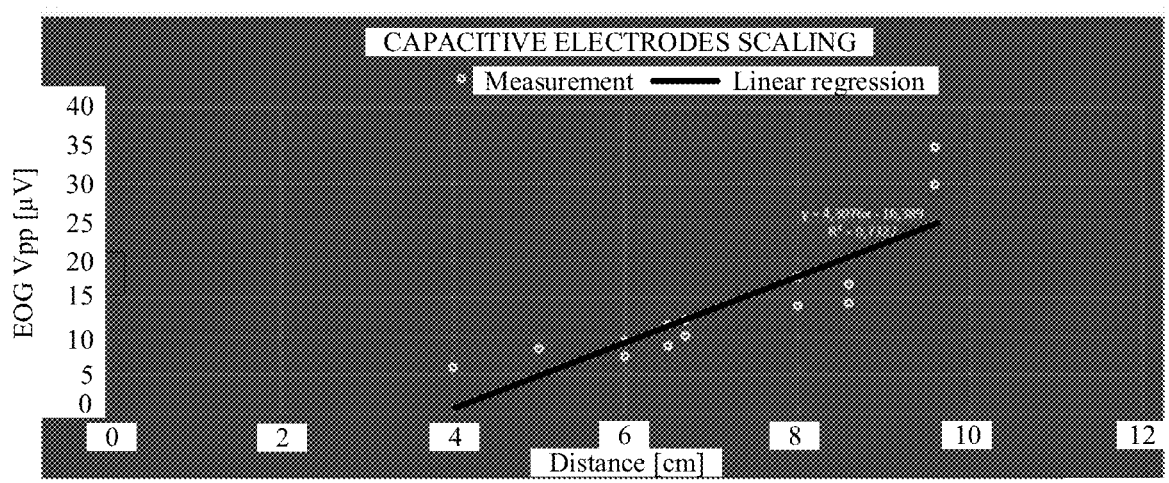
FIG. 6 shows a characterization of unilaterally positioned capacitive electrodes, the graph illustrating measured EOG (peak-to-peak) voltage [mV] versus distance [cm] between electrodes.
Figure 7:
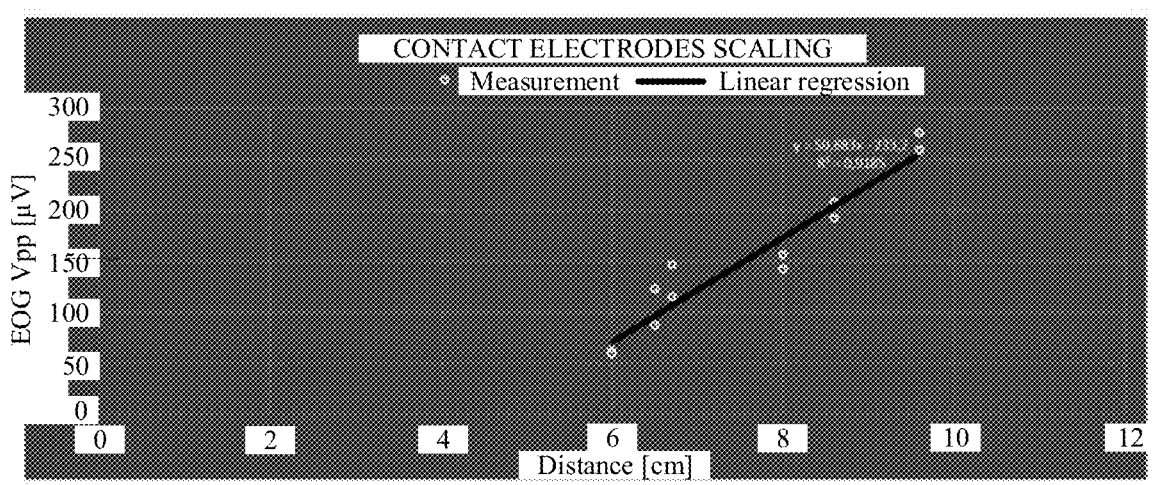
FIG. 7 shows a characterization of unilaterally positioned contact AgCl electrodes, the graph illustrating measured EOG (peak-to-peak) voltage [μV] versus distance [cm] between electrodes, FIG. 8A schematically shows measurement of EOG signals using electrodes on left and right sides of the user's head.

These effects are independent of the kind of electrodes used. In the present work, we have characterised unilateral electrode position configurations and distance scaling for capacitive and contact AgCl electrodes. The characterization consists on a sequential measurement of EOG potentials at different distances between a reference and a sensing electrode. The position of the reference electrode is selected based on the desired final location of the measuring system (e.g. behind the ear) while the initial position of the sensing electrode should be closest to the side of the eyeball. Several measurements can be obtained by shifting the position of the sensing electrode closer to the reference electrode within the plane of the desired eye movement to be captured. The measured potential can be subject to a linear regression to estimate a critical distance for recording EOG. FIG. 6 shows a characterization of unilaterally positioned capacitive electrodes, the graph illustrating measured EOG (peak-to-peak) voltage [mV] versus distance [cm] between electrodes. FIG. 7 shows a characterization of unilaterally positioned contact AgCl electrodes, the graph illustrating measured EOG (peak-to-peak) voltage [μV] versus distance [cm] between electrodes. In both cases, the measured data points have been subject to a linear regression analysis and approximated by a straight line. As appears from the graphs, a critical minimum distance between the electrodes can be defined as the extrapolation of the straight line to its crossing with the distance axis. Below the critical distance, no or very small voltage differences (EOG-signals) are expected. For the capacitive electrodes, a critical distance of approximately 4 cm is implied. For the contact AgCl electrodes, a critical distance of approximately 4 cm is implied. The distance sensitivity (ΔV/Δx) of the EOG signal (where x represents electrode distance) is, however, much larger for the contact capacitive electrodes (~4.3 mV/cm) than for the AgCl electrodes (~51 μV/cm).

The findings of the present disclosure is not limited to any specific type of electrode. It is the assumption that any electrode type can be characterized in this way to obtain a critical distance value for unilateral placement for ear level EOG acquisition.

System and Methods for Calibration of EarEOG Eye-Steering Hearing Device:

People with hearing impairment especially struggle in situations where several (competing) speakers are present (and possibly in the presence of noise from further sound sources). Under such acoustically challenging situations, people with hearing impairment lack a solution to support them to steer/switch their attention. It is possible to use eye gaze to steer an attention beam of a microphone system or to select sound from (e.g. FM or Bluetooth based) wireless microphones. Eye gaze can be picked up by means of electrodes in the ear canal (EarEOG) or elsewhere on the face of a user (see e.g. FIG. 5). The present disclosure proposes a calibration process to transform electrical signals picked up by electrodes attached to the user's head (e.g. at or in the ears or a user) and optional inertial (movement) sensors to relative or absolute eye gaze positions.

Figure 8A:
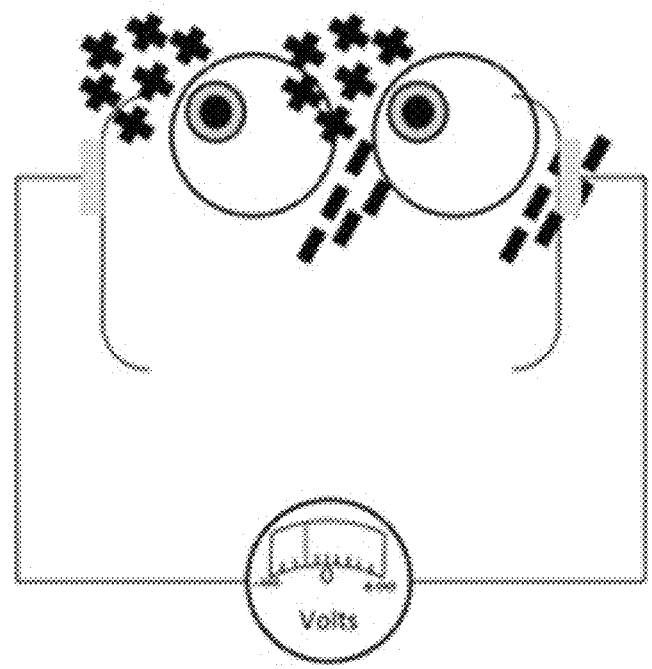
FIG. 8B shows a graph of measured amplitude of EOG signals (from EarEOG electrodes and facial EOG electrodes) versus time for different eye gaze angles.
Figure 8B:
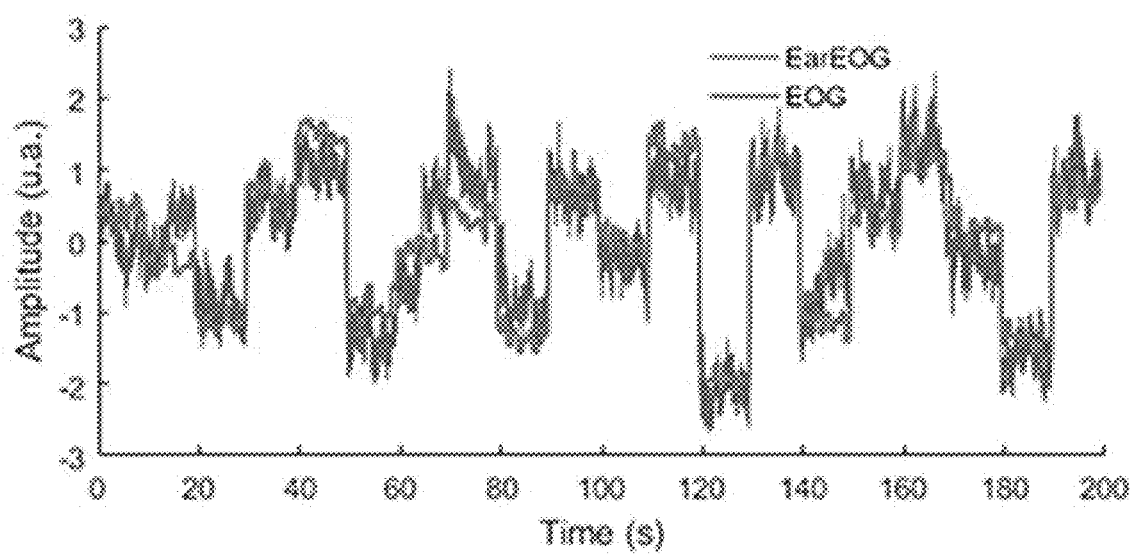

By placing electrodes in the ear-canal we can pick up EOG signals, which provides us with information on where the end-user is looking at (see FIG. 8A, 8B). In order to know where the end-user is looking at, we need to transform the measured values form this in-ear electrodes (V) to an angle (rad or degrees). This present disclosure proposes two methods to calibrate a hearing device comprising EarEOG based control.

FIG. 8A shows measurement of EOG signals using electrodes on left and right sides of the user's head, and FIG. 8B shows a graph of measured amplitude of EOG signals (from EarEOG electrodes and facial EOG electrodes) versus time for different eye gaze angles. FIG. 8A illustrates the electric dipole nature of the human eyes. By placing electrodes on each side of the eyes (e.g. at or in the ears), it is possible to pick up a signal that provide us with information on where the user is looking (e.g. an eye gaze angle).

The EarEOG eye-steering hearing device may consist of the following sensors that are used to calibrate the system:

EarEOG electrodes: These sensors are used to pick up the electric signals indicating where the eyes looking (e.g. gaze angle) at a given point in time. By using information of these sensors alone, it is possible to estimate a relative eye gaze (i.e., angle w.r.t. the head orientation).

Inertial sensors (accelerometer, gyroscope and magnetometer): These sensors may e.g. provide information on a present orientation of the user's head (e.g., rotation of the head, yaw angle). By using information from inertial sensors as well as from the EarEOG electrodes, it is possible to estimate an absolute eye gaze.

Microphones: These sensors collect information on the sound environment. More interestingly, by using several microphones, we can calculate direction of arrival of sound sources. The direction of arrival of sound sources can be used in an on-the-fly calibration/recalibration process, with the assumption that the user eventually looks at the sound source.

In the present disclosure, two methods for calibrating such system are proposed:

1) Static calibration: This method takes advantage of using an external device to calibrate the system. Such calibration procedure may be performed in a controlled acoustic environment, e.g. in an audiology clinic, or at home.

2) Dynamic calibration: This method may be used to calibrate/re-calibrate the system while being in dynamic situations during use of the hearing device (e.g., while the user is moving in a multi-talker environment).

Figure 9A:
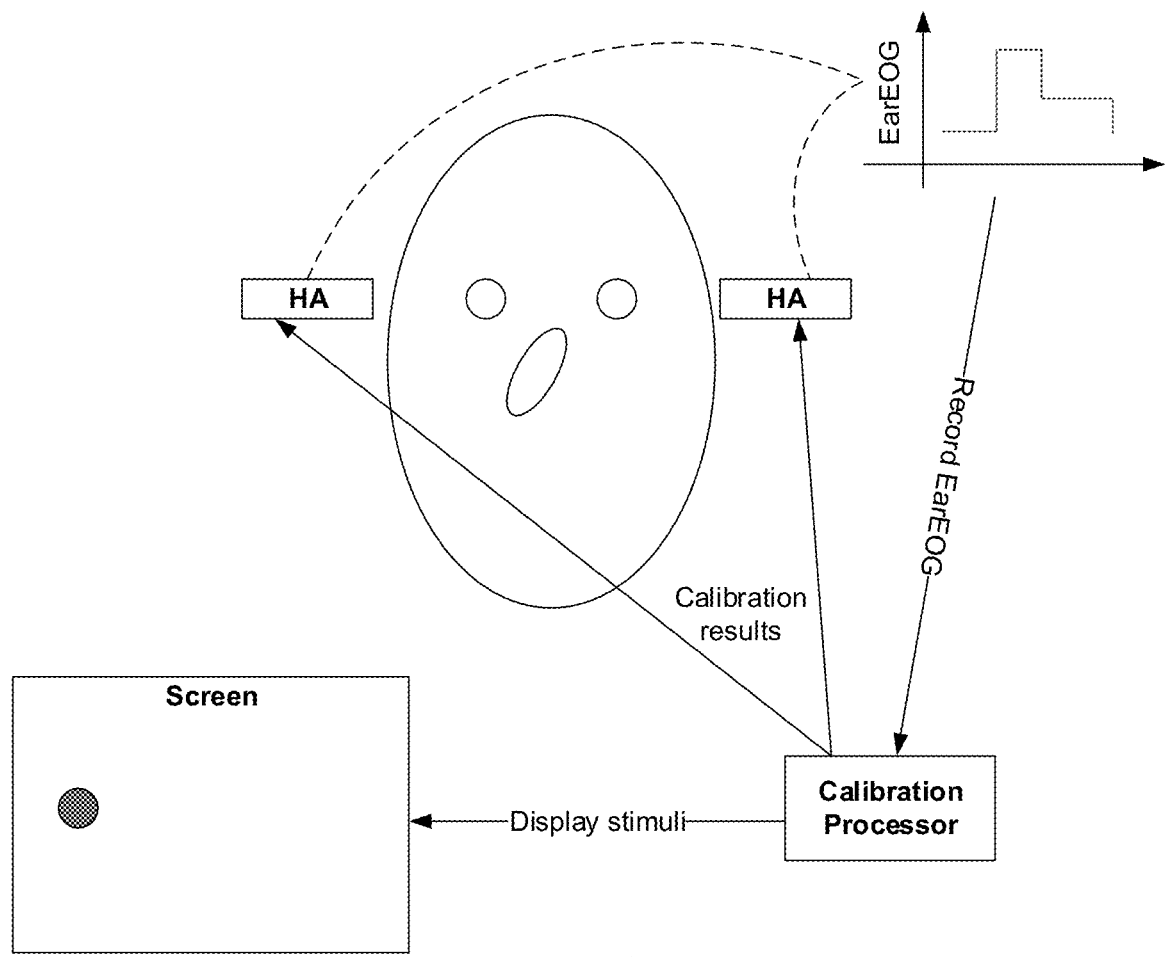
FIG. 9A schematically illustrates an overview of a static calibration method of a hearing device providing an EOG-signal according to the present disclosure.

Static Calibration:

An overview of the system required for this static/controlled calibration method is shown in FIG. 9A. The system is composed by the following elements:

1) The EarEEG hearing device is worn by the user/person with hearing impairment and measures the EarEOG signals of the wearer of the system as well as the head orientation through inertial sensors (yaw angle).

2) An external screen is used to present/display a calibration sequence that the user is supposed to follow with the eye gaze.

3) Calibration processors is responsible of collecting EarEOG data from the EarEOG hearing device, motion sensor data from the hearing device, as well as sending predefined stimuli calibration sequences to the Screen, generating a calibration data set by doing analysis on both types of data (EarEOG+Inertial Sensor & stimuli position) and sending this calibration results to the EarEOG hearing device.

This system could potentially be embedded in a smartphone APP but it could also form part of a fixed set-up in an audiology clinic.

The steps needed to calibrate the EarEOG hearing device are the following:

1) The user is wearing an EarEOG hearing device

2) The user is positioned in a specific location in front of a screen at a certain distance from his eyes. In case of using a smartphone, this distance could be estimated from the frontal camera of the device.

3) The user is instructed to follow with the eyes a signal on the screen (e.g., red dot) while keeping the head still or while moving the head naturally. In the head natural condition, the head the orientation is tracked by the inertial sensors of the device or if using a smartphone, from the frontal camera of the smartphone.

4) A calibration sequence starts, where a dot starts moving in the screen. The sequence is a combination of fast transitions between locations (in eye literature this is known as saccades) and staying still in certain locations (in eye literature this is known as fixation).

5) While the sequence takes place, the EarEOG device collects data from electrodes together with the location of the dot (x,y)

6) At the end of this sequence, the synchronized EarEOG+Inertial Sensors data and DotLocation are used in a calibration process to be able to estimate the eye gaze, e.g. eye gaze angle.

7) The results of the calibration process are then uploaded to the EarEOG hearing device.

Figure 9B:
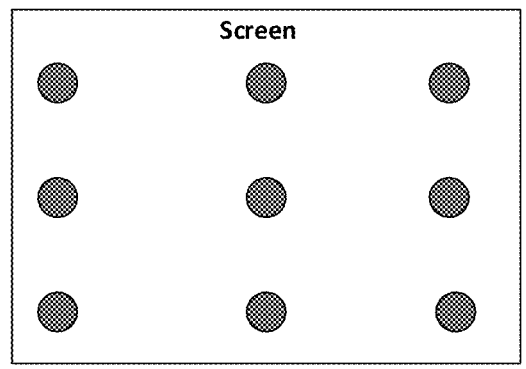
FIG. 9B shows an example of calibration sequence, FIG. 10 schematically illustrates a dynamic calibration process, which can be used in an acoustic scenario where at least one sound source is present and where it is assumed that the user looks at that sound source at a specific point in time.

FIG. 9B shows an example of a calibration sequence, in particular an example of the positions a calibration sequence may cover. Note that the dot location varies both on horizontal axis but also on the vertical axis.

Dynamic Calibration

Figure 10:
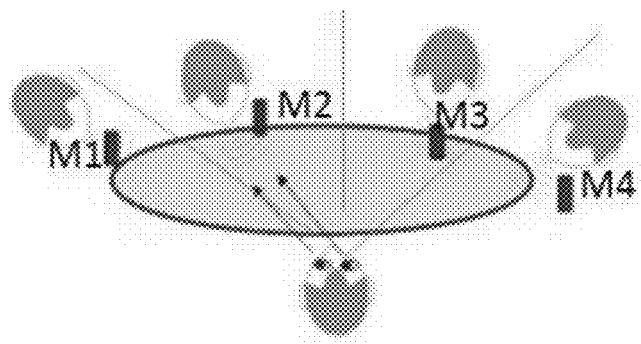

FIG. 10 schematically illustrates a dynamic calibration process, which can be used in an acoustic scenario where at least one sound source is present and where it is assumed that the user looks at that sound source at a specific point in time.

While the above introduced (static) method requires external devices and a more complex set-up, the dynamic calibration uses assumptions to simplify the process. Current hearing aids use their microphone and algorithms to detect the direction of arrival (DoA) of a sound source. As the position of microphones/hearing aids is fixed on the head, DoA algorithms can provide an estimate of the angle where the sound is coming from. If we then assume that at certain moments the end-user looks at those sound sources, we have a calibration point by comparing the DoA angle provided by the microphone data with the EarEOG data.

Simultaneous Localization and Mapping (SLAM)

Figure 11:
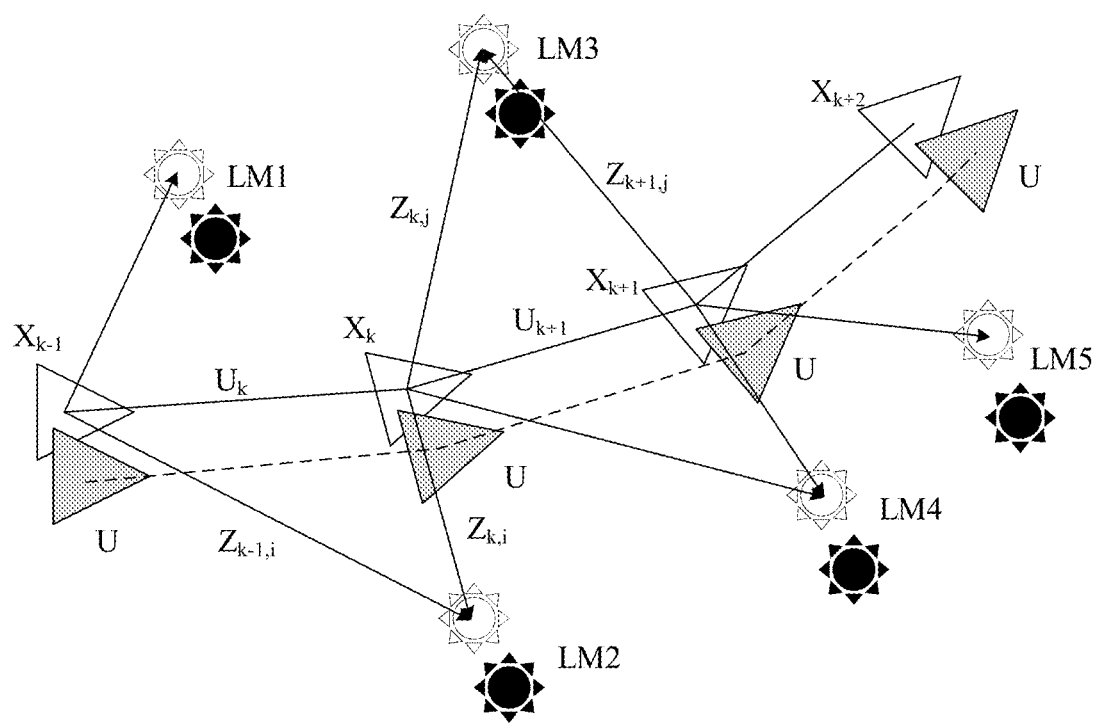
FIG. 11 illustrates the scheme of simultaneous localization and mapping (SLAM)

SLAM relates to a computational problem typically used in self-driving cars, where a map of relevant landmarks is constructed/updated while at the same time keeping track of the location of the agent (e.g., car) within that map. This scenario is illustrated in FIG. 11.

If the SLAM problem is translated into the acoustic domain, the user would be navigating in a map of sound sources. The SLAM algorithm would then try to construct/update a map of sound sources and ubicate the end-user in that map. In order to solve this problem, data from the hearing device microphones, EarEOG and IMUs, are needed.

The proposed dynamic calibration process would make use of this sound source map and the user location in this map to calibrate/re-calibrate the EarEOG device. This would be done by assuming that in certain moments, the user is looking at the sound sources. For each time we make this assumption, we then have a calibration point.

The success of this dynamic calibration process relies on whether the assumption on the user looking at a sound source at a given point in time holds. When the user switch attention to a new sound source located in the right, he/she does the following steps:

1) Fast saccade from the original target to the new target: eyes going right. This usually takes around 150 ms.

2) Once the eyes are almost on the target, then the head starts rotating towards the target, hence the head starts rotating right.

3) While the head is rotating, the eye are fixating into the target but since the head is rotating, the eyes then compensate for the head rotation and move left. This simultaneous head/eye movement is quite particular because
   a. Both eye/head go at the same speed (to counteract each other)
   b. Both signals have opposite direction (eyes compensate head movement) 4) Once the head reach its 'final destination', both eye and head remain fixed for a period of time.

If a the recorded EOG signal reflect the above process, the assumption that the user is looking at a new sound source can be trusted (high confidence). If not, the assumption cannot be trusted (low confidence).

Figure 12:
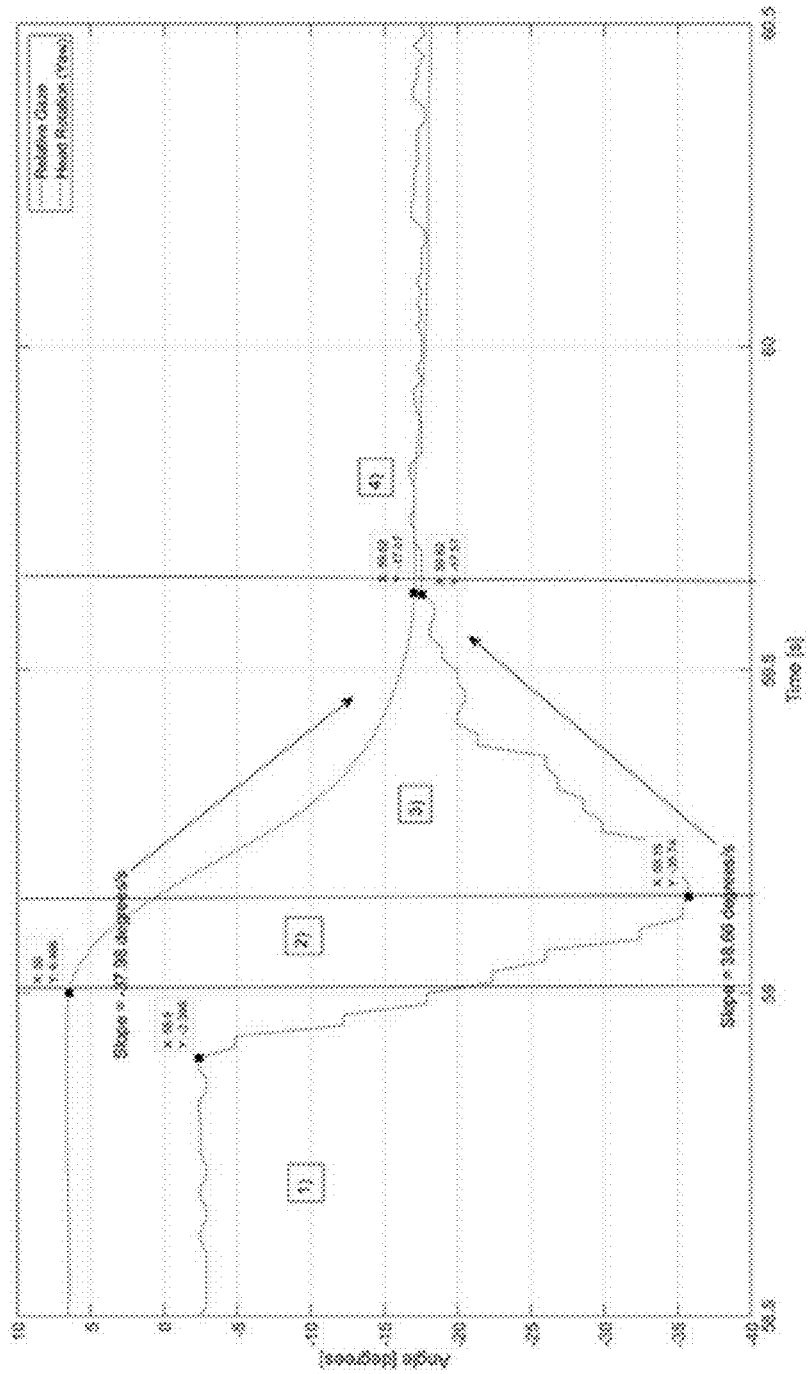
FIG. 12 shows the different steps mentioned above as reflected in recorded data of a user, FIG. 13 schematically illustrates a middle-ear reflex activated by vocalization.

FIG. 12 shows the different steps mentioned above as reflected in recorded data of a user. Steps required to detect when the end-user is switching attention to a new target. The Y-axis shows the eye gaze angle in degrees [°] and the X-axis shows time [s]. The piecewise linear graph (starting bottom left) illustrates Eye Gaze angle versus time (recorded using an eye-tracker) and the smooth graph starting top left illustrates head rotation angle versus time (recorded using inertial sensors). The different steps, 1)-4), of the above-mentioned 'attention-shifting procedure' are indicated in FIG. 12. Note that the slopes of the two graphs (between 59 and 59.5 s) in step 3) are almost equal and of opposite sign (as indicated by the two solid arrows in FIG. 12).

When the signals from the inertial and EarEOG sensors indicate that there is such pattern we can assume that the end-user is looking at a new object. If at the same time a sound source emits sound, a direction of arrival (DOA) may be estimated from sound signals received by microphones (e.g. of the hearing device), and a new calibration point can be added by correlating EarEOG data, Inertial sensor data and DoA data.

The below pseudo code summarizes the steps of the above described procedure.

```
while DynamicCalibration.running( )
    % Run SLAM
    [new_map, new_location] = SLAM( )
    % Assumption met? Eye&head direction, same speed
    %opposite direction + fixation + active sound source
    if assumption.happens( )
        DynamicCalibration.addPoint( )
    end
    if DynamicCalibration.enoughPoints( )
        DynamicCalibration.calibrate( )
    end
end
```

Mathematical Formulation:

The equations below show the calculations to run when doing the online calibrations process. If we get a set of (n) DoA measurements corresponding to a smaller number of directions (m) then we can put all these in a matrix Y (mxn). If we also have measured (n) fixations from EOG with corresponding (m) directions, we collect this in another matrix A (mxn). It is then assumed that the each DOA is paired with the corresponding fixation from EOG, we then have that $$Y = \alpha A$$

$$\hat{\alpha} = Y^*(A^*A^*)^{-1}$$

where α is the sought scale and â is the least squares estimate. For the equation above to hold, both DoA and EOG measurements should be in the same global coordinate framework (or at least a known one so that we can then apply corresponding rotation).

EEG and EOG:

EOG signals may typically be captured by electrodes/sensors adapted to pick up brain wave signals (Electroencephalography (EEG)). The EOG signals can be seen as artefacts in the (typically weaker) EEG-signals. The capture of EEG signals and EOG signals can thus be provided by the same electrodes/sensors. The two kinds of signals can be separated in subsequent signal processing steps.

In the following a number of features relating to EEG-electrodes and EEG signals are disclosed. The EEG-features can be exploited alone or in combination with EOG-features.

Detection of Middle-Ear Reflex with EEG:

The middle-ear reflex is activated either by loud sounds or by vocalization. It activates the stapedial muscle and tensor tympany causing less sound to be transmitted to the inner ear.

Figure 13:
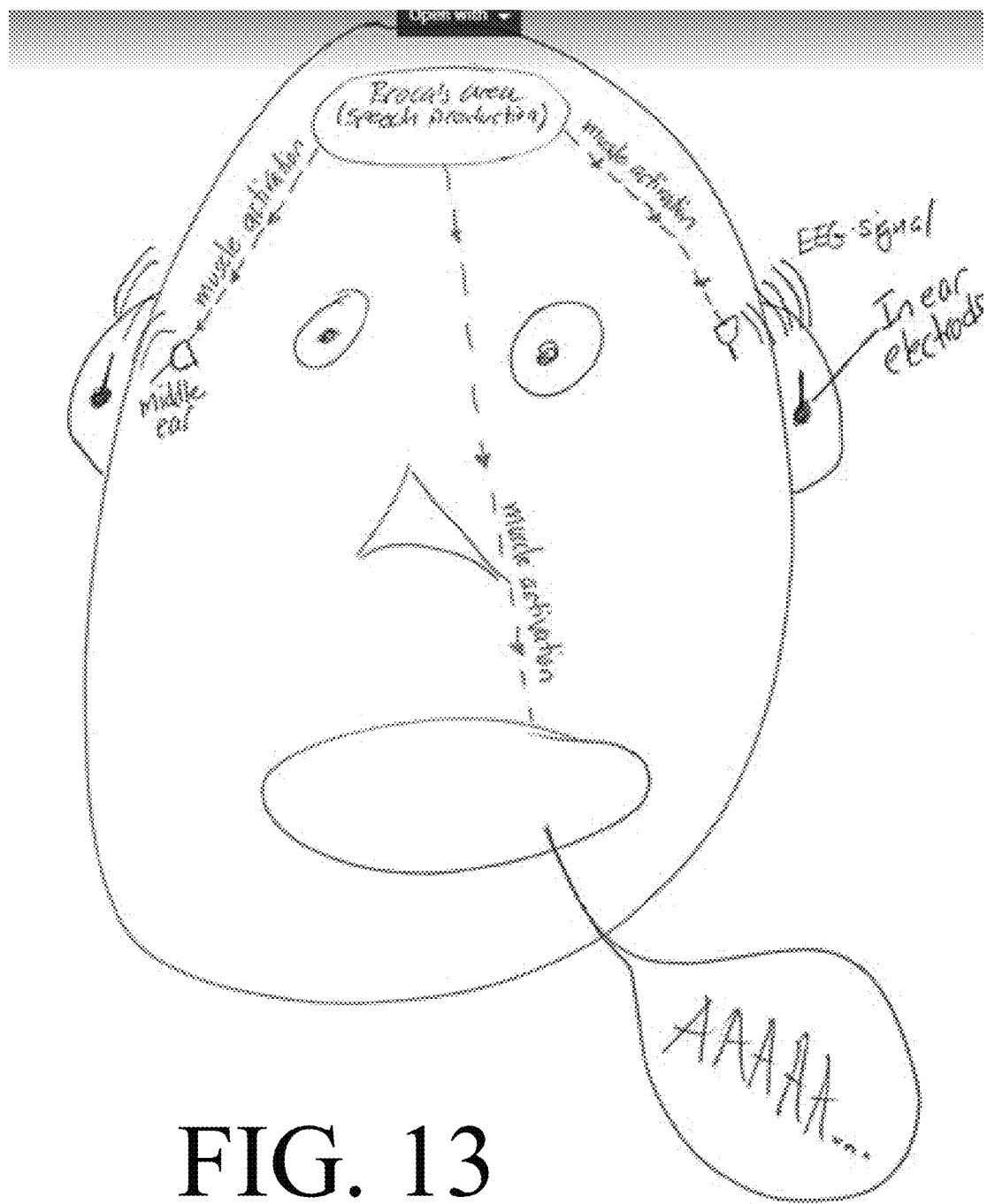

Such muscle activity can be detected by EEG and used in the hearing aid to apply signal processing specifically designed for use when the middle-ear reflex is active. FIG. 13 schematically illustrates the middle-ear reflex activated by vocalization.

Users of hearing aids often complain that own voice perception (OVP) is different when wearing hearing aids. In addition, users are sensitive to so-called occlusion (loudness increase of low frequency sounds). Considerable efforts have gone into improving OVP and reducing occlusion. So far, success has been limited. This may be because own voice detectors have been based on microphones only (acoustic detection) and therefore inherently lagging. Given that immediately before vocalization, the middle ear reflex is activated in humans [5] detecting activation of the middle ear reflex with EEG would provide much earlier own voice detection. Potentially such detection can facilitate signal processing which would improve OVP. Such detection mechanism might also be applied for mechanisms aimed at reducing occlusion (e.g. a mechanically adjustable vent which may be controlled by the hearing aid processor).

In addition, detecting middle-ear reflex activation by sound stimulation may have additional applications. This includes the possibility of early own voice detection as a means to improve the processing with respect to signal to noise estimates and directional processing of incoming sound. Directional processing is intended to enhance external sounds and this is negatively influenced by own voice signals.

In an aspect of the present disclosure, a hearing aid comprising in-ear electrodes configured to pick up body signals is configured to detect the middle ear reflex. The hearing aid may comprise a processor configured to modify its frequency response according to user preference based on said detection of the middle ear reflex. The processor may be configured to detect an onset of a user's own voice based on said detection of the middle ear reflex. The processor may be configured to control a controllable vent in dependence of said onset of a user's own voice. Such modification could be based on the suggestion in [5] whereby gain is reduced to about half compared to the gain applied in the absence of own vocalization.

Electrophysiological Time-Stamping for Naturalistic Portable EarEEG Systems

Several electrophysiological signals have been established as indicators of cognitive processes happening as a result of defined and controlled experimental stimulation. The P300, N400, and the mismatch negativity (MMN) among others, for example, reflect cognitive processing of unexpected events or rule violations. Brain wave analysis, particularly alpha wave oscillations, has also been established as indicator of cognitive load, meaning how much work the brain is exerting on a given task.

These signals can be evaluated with electroencephalography (EEG) recorded either from the scalp or from within the ear with earEEG electrodes. However, as part of the signal processing required to obtain the responses, a time-stamp coupled to each stimulus presentation need to be available. This controlled stimulus presentation would not be available in an uncontrolled naturalistic environment.

A portable EEG system aiming for the evaluation of cognitive processed under naturalistic environments either with scalp EEG or earEEG will require a time-stamp signal to process.

It has been shown in research that when the EEG is averaged time-locked to blinks, and the part of the potential that is proportional to the electrooculogram (EOG) is subtracted, a signal (the 'residuum') remains which resembles an event-related potential (ERP). While some information in this ERP is related to the visual perception of light, it has also been shown that information contained between eye-blinks can reflect cognitive task relevant cognitive processes.

In an aspect of the present disclosure, there is provided a portable EEG system, either coupled with a hearing instrument or in a stand-alone configuration, that provides information on the real-life cognitive processes by using eye-blinks as a time-stamping signal to process electrophysiological data.

The system is comprised of (see FIG. 1):

1. EEG sensors either placed on the scalp or in and around the ear cavity.

2. An EEG amplifier that records the differential input form from the sensors.

3. An eyeblink detector that detects when an eyeblink event has occurred.

Figure 14:
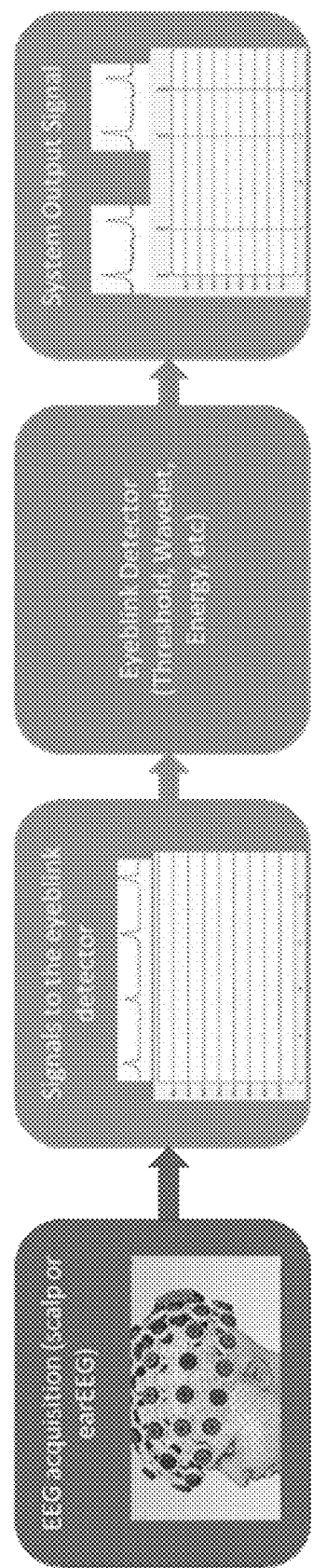
FIG. 14 shows an overview of an electrophysiological time-stamping system for EEG signals.

FIG. 14 shows an overview of an electrophysiological time-stamping system for EEG signals. The output of the system is the raw EEG recorded signal time-stamped at the points where the eye-blinks were detected cf. rightmost box denoted 'System Output Signal' in FIG. 14. The four peaks in the top graph indicate the timing of eye blinks These points in time are indicted in the lower EEG-channel signals by vertical lines. This signal can be used for post-processing depending on the application desired which could be but is not limited to:

Mental Load
Fatigue
Auditory evoked potentials
Visual evoked potentials

The recorded scalp or in-ear EEG locked to the eyeblinks can then be averaged synchronized with respect to the eyeblinks to derive Event Related Responses (ERPs) that may reflect information about cognitive process taking place [6].

Eye Blinks as an Indicator of Fatigue and Mental Load in Real-Life Environment Using a Portable Eye-Blink Detector.

The detection of the loss of alertness can be important in everyday life (e.g. when driving a car or when being at work). Eye blinking is a psychophysiological measure which has been demonstrated to be connected to cognition and mental fatigue. The use of Electroencephalographic Activity (EEG), Electrooculographic (EOG) techniques, eye activity measures using eye-tracking cameras have been proposed as methods for objective alertness and fatigue monitoring. It has been used in various different contexts aiming at monitoring the participants' performance and fatigue level and for detecting a loss in alertness. Furthermore, literature indicate that the use of eye blink measurement in "noisy" complex environments can be used as both a feasible and valuable assessment technique of work load [7]. It appears to be an inverse relation between difficulty of task and eye blinking frequency [6], whereas the eye-blink frequency increase with time on task and mental fatigue.

The following (portable) devices can be used for the eye-blink frequency:

EarEEG
EOG
EEG
Infrared eye-tracking camera
Video camera

In an aspect of the present disclosure a portable system that can detect eye-blinks (EOG, EEG, eye-tracking camera, video camera) and which can be coupled with a hearing device is provided. The idea is to measure the eye blink frequency individually during every day live (e.g. when working at the monitor, being at work or when driving a car). Since each person has an individual eye blinking frequency with individual variability of varying degree, the baseline blink frequency needs to be established individually first. Second, an eye-blink detector, which uses the raw data form the portable device (either earEEG, scalp EEG, or an eye-tracker), is then detecting changes in the blink frequency. As soon as the frequency changes and reach a critical threshold, this shall be monitored with the detector. Significant changes in the blink rate can then be used as an indicator of either change of:

Mental Load
Fatigue/loss of alertness

A feedback is then sent to the user, which can be of different kinds. It can be either a direct information to the user (at the end of a day) about the fatigue level. Another way would be to give feedback to the hearing device when the blink rate hits a certain threshold. As a consequence thereof, the device may adapt and change its processing (such as the noise reduction (NR) scheme) in order to adapt to the fatigue level/mental load of the user (see e.g. [8]).

Figure 15:
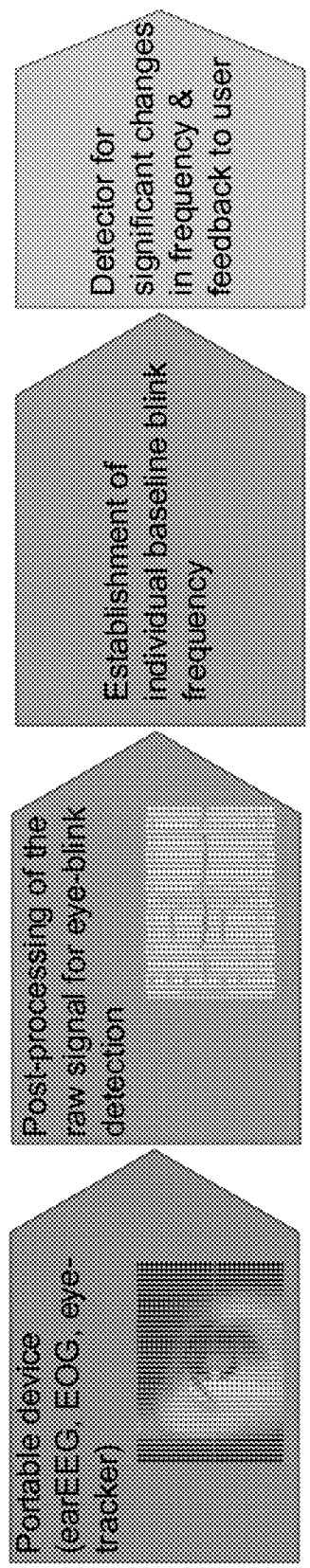
FIG. 15 shows basic steps of an eye blink detector.

FIG. 15 illustrates the basic steps of an eye blink detector or corresponding components of a blink detector system. The system comprises:

1. $1^{st}$ box from the left: A sensor from which eye-blinks are detectable: This sensor can be placed in or around the ear such as earEEG electrodes or EOG electrodes; The sensor can also be worn around or above the eyes such as an infrared camera, or video camera mounted in eye-frames.

2. $2^{nd}$ box from the left: An eyeblink detection module for postprocessing of the sensor signal and whose output is the eye-blink rate (i.e. number of blinks in a window of time) 3. $3^{rd}$ box from the left: An eyeblink profile module that will assess the individual eye-blink baseline at idle times and evaluate the current eye-blink rate against the stablished rules for categorization of mental load or fatigue 4. 4$^{th}$ box from the left: A coupling link to a hearing instrument to provide feedback on the final state decision to the user and/or the hearing device to change its processing.

Unsupervised EEG/Audio Translation:

In a further aspect, a scheme for high-accuracy and fast classification of attended source, given audio and EEG (electroencephalography) input is provided by the present disclosure. A number of studies in the auditory literature have attempted to provide a highly performing, speech tracking computational algorithm, framed at deciphering auditory attention, i.e. identifying the sound source of the listener's interest in a mixture of competing sources.

Common to most of these computational algorithms is that they rely on regression framework, and in particular linear regression (LR) solved using least squares (LS), benefitting from linear relations between EEG and audio data. Depending on a mapping direction, forward (audio→EEG) or inverse (EEG→audio), we distinguish two paradigms—encoding and decoding—supervised cases of forward and inverse mappings, respectively, with the decoding algorithms receiving the greatest attention in the literature. Especially prominent decoding algorithm is stimulus reconstruction (SR), where the sound stimuli are estimated/reconstructed from the measured neural responses. In addition, few studies considered the forward mappings and encoding algorithms. More recently, a combination of encoding and decoding was proposed, and canonical correlation analysis (CCA) was used in parameter optimization.

In general, the approaches found in the current literature rely solely on the supervised learning and hand-engineered, class-specific feature extraction from labelled data, and require human ingenuity and prior knowledge to discover good features/representations.

The main shortcomings of these studies are low performances, in terms of classification accuracy rates, and long time needed to make a decision on the attended sound source. We do not have ~100% classification accuracy rates yet. The additional problem is that classification is not instantaneous, i.e., long time is needed to make a decision on attended sound source, where we still need tens of seconds to have satisfactorily high classification rates (>80%), which is not desired for real-time systems. One explanation for these low performances is that we do not yet have the representation (features), which can describe EEG-audio relations sufficiently well. For these reasons, there is a need for a different view at EEG-audio data and thus, a different approach to solving this problem.

Unsupervised learning build a high-level representation from un-labelled data. Recently, deep learning reached impressive performances from breakthrough in unsupervised learning in neural machine translation and speech recognition. In unsupervised learning in neural machine translation, two training strategies have been used, namely back translation and denoising. In back translation, the sentence/speech segment is translated from one language (L1) to another (L2), e.g. French→English, and then the translated sentence is translated back to L1. If the original and back-translated sentences are not identical, the neural network (NN) is adjusted so that when translating the same sentence from L1 to L2 next time, the two become closer. Denoising is similar to back translation, but do not translate from L1 to L2, and instead noise is added by removing/rearing the order of the words to a sentence in one language and an attempt to translate such sentence to the original language is made. Such learning can be generalized to new languages, such as EEG-audio languages, by utilizing communalities in different languages.

In this aspect, the main idea is that our signals (Audio and EEG) shall be interpreted as different "languages" that must include communalities since there are correlations between the signals. The task for the system is to, by unsupervised learning, uncover these communalities.

Unsupervised learning can capture relevant information about EEG/audio 'language' pairs, so as to extract good features explaining how audio is correlated with EEG, or more precisely, explaining how neural processes govern selective attention, from the available data without human assistance, i.e. without labelling the data. Here we aim to use deep unsupervised learning to build an encoder-decoder model of the EEG/audio data (2 different 'languages') to identify the common good latent structure-features. By learning to reconstruct both EEG and audio data from the common feature space, we suppose that our model will use the knowledge it has already acquired to interpret the new incoming EEG/audio, identify good features and classify the speech stream from the attended talker without using any labelled data.

Deep Learning: We propose few different systems for audio/EEG translation. The first system we propose follows an encoder-decoder architecture with an attention mechanism (addressing the limitations of encoder-decoder architecture on longer data sequences); similar to what is typically used in NMT (neural machine translation) systems. The core of our EEG/audio translation system involves training a large deep neural network (DNN) with some variant of feedforward (acyclic) NN (FNN) and recurrent (cyclic) NN (RNN). Some of the FNN variants we will use are convolutional NN (CNN) and improved CNNs (e.g. GPUCNN (Graphics Processing Unit CNN), MP (Max-Pooling) CNN, GPU-MPCNN, etc.). Some of the RNN variants we will use in encoders and decoders are LSTM (long short-term memory) and (deep) bidirectional RNN and LSTM, etc., on data pairs.

The second system we propose is based on deep canonical correlation analysis (DCCA), a DNN extension of CCA. Contrary to the first system, where the training criteria is to learn a representation that best 'reconstructs' the audio/EEG inputs, DCCA tries to learn the representations/features in both 'languages' that are maximally correlated.

We also combine DCCA with auto/shared encoder-decoder architecture in our third system, so as to overcome the drawbacks of the first two system (if any) and to obtain the best results on audio/EEG language translation and deciphering the auditory attention.

Overview of our suggested method: We consider a dataset of audio segments, denoted by $D_{aud}$, and another dataset of EEG segments, denoted by $D_{EEG}$. Datasets $D_{aud}$ and $D_{EEG}$ do not necessarily need to correspond to each other. We propose two different approaches to EEG/audio attention translation system, with the difference having either (1) autoencoders—one encoder for $D_{EEG}$ and one encoder for $D_{aud}$, or (2) having one and only one shared encoder—the same encoder is used for both directions—EEG→audio and audio→EEG. After the model start in a naive manner (segment-by segment translation of EEG/audio), at each next iteration, these auto/shared encoders and decoders are trained to minimize an objective function, measuring their capacity to reconstruct and/or to learn representation in two languages that are maximally correlated and to translate from the incoming 'noisy' form of EEG/audio data segments. To be able to do this training in a completely unsupervised manner, we use two strategies, namely denoising and back translation (see below). These two techniques combined together can teach us more a deeper structure of t EEG/audio data and provides us with good features that can be used later used in attention classification task.

Denoising: If we do not impose any constraint, the auto/shared encoder will promptly learn to just copy each incoming segment one by one, without learning any useful structure and finding good features in the data. To prevent this, we add noise to the incoming data. The idea is to randomize EEG and/or audio sub-segments, and let the system reconstruct the incoming EEG or audio segment. With this approach, the system will learn more about the internal structure of audio and EEG languages.

Back translation is similar to denoising, except that here, we translate segment in one language to another, and then translate the translated version back to original language. If the original and back-translated segments are not identical, the NNs are adjusted so that we get closer translation in next iteration. Throughout the training, we alternate between these techniques and strategies from segment to segment. During each iteration, we would perform denoising for EEG and audio segments and two back-translations (one from EEG to audio and one from audio to EEG). The newly learnt auto/shared encoder(s) and decoders would then be used at next to produce new translations between EEG and audio segments, until convergence.

After training and learning the relevant features and translating from EEG to audio data and vice versa), we will also decipher auditory attention, i.e. we will classify the attended sound source. To do this, we propose several simple classifiers that will act as our learned features to classify auditory attention: (1) conventional non-linear machine learning methods such as kernel machines, (2) linear methods such as linear discriminant analysis (LDA), or forward/backward modelling and CCA, or (3) deep neural networks.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein but are to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

[1] Nan Zhang, Wei-Long Zheng, Wei Liu, and Bao-Liang Lu. 2016. Continuous Vigilance Estimation Using LSTM Neural Networks. In Proceedings of the 23rd International Conference on Neural Information Processing—Volume 9948, Akira Hirose, Seiichi Ozawa, Kenji Doya, Kazushi Ikeda, Minho Lee, and Derong Liu (Eds.), Vol. 9948. Springer-Verlag, Berlin, Heidelberg, 530-537. DOI: https://doi.org/10.1007/978-3-319-46672-9 59.

[2] US20180368722A1 (Oticon) 27 Dec. 2018.

[3] EP3185590A1 (Oticon) 28 Jun. 2017.

[4] [Borg & Zakrisson; 1975] 1. E. Borg & J.-E. Zakrisson (1975) The Activity of the Stapedius Muscle in Man During Vocalization, Acta Oto-Laryngologica, 79:3-6, pp. 325-333, DOI: https://doi.org/10.3109/00016487509124694.

[5] [Laugesen et al.; 2008] Soren Laugesen, Niels Sogaard Jensen, Patrick Maas, and Claus Nielsen, "Self-perceived Own-Voice Level and Sound Quality in Hearing Aid Users", Hearing Review, Jan. 4, 2008 (DOI: https://www.hearingreview.com/practice-building/practice-management/self-perceived-own-voice-level-and-sound-quality-in-hearing-aid-users).

[6] Wascher, Heppner and Hoffmann, "Towards the measurement of event-related EEF activity in real-life environments", International Journal of Psychophysiology 91 (2014) pp. 3-9.

[7] [Stern and Skelly; 1984] John A. Stern, June J. Skelly "The Eye Blink and Workload Considerations", In Human Factors and Ergonomics Society Annual Meeting Proceedings 28(11): pp. 942-944 (1984). DOI: 10.1177/154193128402801101

[8] US2010196861A1 (Oticon) 05 Aug. 2010

The invention claimed is:

1. A method for picking up body signals from the head of a user, the method comprising:
    placing first and second electrodes on first and second different positions at a first side of the user's head in direct or capacitive contact with the user's head, said first side comprising a first eye of the user, the first and second electrodes being configured to pick up first and second electric potentials, respectively, from the user's body; and
    providing an Electrooculography signal representative of a corneo-retinal potential difference of said first eye of the user in dependence of said at first and second electric potentials, representing horizontal eye gaze,
    wherein the first and second electrodes are located in a plane of horizontal eye movements when the user is in an upright position.

2. A method according to claim 1 wherein the first position is closer to the first eye than the second position.

3. A method according to claim 1 wherein the first and second positions are on each side of the ear.

4. A method according to claim 1 wherein the first and second electrodes are capacitively coupled electrodes.

5. A method according to claim 1 wherein the first and second electrodes are direct contact electrodes.

6. A method according to claim 1 wherein the first and/or second electrodes are implanted in the head of the user.

7. A method according to claim 1 wherein the first and second positions are located a distance $L_{12,min}$ from each other.

8. A method according to claim 7 wherein the electrodes are calibrated to determine the sensitivity of the electric potential picked up by the second electrode to its distance from the first electrode.

9. A method according to claim 7 wherein the distance between the first and second electrodes when located on the user's head is in the range between 3 cm and 5 cm.

10. A portable electronic device comprising
first and second electrodes configured to be located on first and second different positions at a first side of the user's head in direct or capacitive contact with the user's head, said first side comprising a first eye of the user, the first and second electrodes being configured to pick up first and second electric potentials, respectively, from the user's body, and
a processor electrically connected to said first and second electrodes and configured to provide an Electrooculography signal representative of a corneo-retinal potential difference of said first eye of the user in dependence of said at first and second electric potentials, representing horizontal eye gaze,
wherein the first and second positions are located substantially in a plane through the first and second eyes of the user.

11. A portable electronic device according to claim 10 configured to use said Electrooculography signal to monitor eye movements of the user.

12. A portable electronic device according to claim 10 configured to monitor one or more of a user's
Vigilance, and
Balance disorder.

13. A portable electronic device according to claim 10 comprising antenna and transceiver circuitry configured to transmit said Electrooculography signal or a signal derived therefrom to another device or system.

14. A portable device according to claim 10 comprising a head-worn frame for supporting one or more sensors.

15. A method according to claim 14 wherein said head-worn frame is configured to support glasses.

16. A method according to claim 14 wherein said one or more sensors comprises a light-based image sensor.

17. A hearing device comprising or forming part of a portable electronic device according to claim 8, the hearing device being configured to be located in or at an ear of a user or to be partially or fully implanted in the head of the user, the hearing device comprising:
an input unit comprising an input transducer configured to pick up sound from the environment of the user and to provide an electric input signal representative of said sound; and
an output unit configured to present stimuli perceivable to the user as representing said sound or a processed version thereof,
wherein functionality of said hearing device is partially or fully controlled by said Electrooculography signal.

18. A hearing device according to claim 17 wherein said input unit comprises at least two input transducers configured to pick up sound from the environment of the user and to provide respective at least two electric input signals; and wherein said hearing device further comprises a processor for processing said at least two electric input signals; and wherein said processor comprises a beamformer for providing a beamformed signal based on said at least two electric input signals, and wherein said processor is configured to partially or fully control said beamformed signal in dependence of said Electrooculography signal.

19. A hearing device according to claim 17 comprising a further electrode located in or on a housing of the hearing device.

20. A hearing device according to claim 17 being constituted by or comprising a hearing aid, a headset, an earphone, an ear protection device or a combination thereof.

21. A hearing device according to claim 17 being constituted by or comprising an air-conduction type hearing aid, a bone-conduction type hearing aid, a cochlear implant type hearing aid, or a combination thereof.

22. A binaural hearing system comprising first and second hearing devices as claimed in claim 17, wherein the first and second hearing devices are configured to be able to exchange data between each other.

* * * * *